United States Patent
Miller et al.

(10) Patent No.: US 10,147,189 B2
(45) Date of Patent: Dec. 4, 2018

(54) GROSS FEATURE RECOGNITION OF ANATOMICAL IMAGES BASED ON ATLAS GRID

(71) Applicant: The Johns Hopkins University, Baltimore, MD (US)

(72) Inventors: Michael I. Miller, Pikesville, MD (US); Susumu Mori, Ellicott City, MD (US); Kenichi Oishi, Lutherville-Timonium, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/101,779

(22) PCT Filed: Dec. 8, 2014

(86) PCT No.: PCT/US2014/069158
§ 371 (c)(1),
(2) Date: Jun. 3, 2016

(87) PCT Pub. No.: WO2015/085319
PCT Pub. Date: Jun. 11, 2015

(65) Prior Publication Data
US 2016/0307319 A1    Oct. 20, 2016

Related U.S. Application Data

(60) Provisional application No. 61/913,146, filed on Dec. 6, 2013.

(51) Int. Cl.
*G06K 9/00*    (2006.01)
*G06T 7/00*    (2017.01)
(Continued)

(52) U.S. Cl.
CPC .......... *G06T 7/0014* (2013.01); *A61B 5/0037* (2013.01); *A61B 5/0042* (2013.01);
(Continued)

(58) Field of Classification Search
CPC . G06T 7/32; G06T 7/11; G06T 7/0012; G06T 7/0014; G06T 7/337;
(Continued)

(56) References Cited

U.S. PATENT DOCUMENTS 6,430,430 B1 *  8/2002  Gosche ............... G06T 7/0012
                                              128/920
8,774,482 B2 *  7/2014  Reisman ............. G06T 7/0028
                                              132/128

(Continued)

FOREIGN PATENT DOCUMENTS

WO    03/021284 A1    3/2003
WO    2008/139167 A2   11/2008
(Continued)

OTHER PUBLICATIONS

Bai et al., "Effectiveness of the Finite Impulse Response Model in Content-Based fMRI Image Retrieval," pp. 743-750.
(Continued)

*Primary Examiner* — Ali Bayat
(74) *Attorney, Agent, or Firm* — Venable LLP; Henry J. Daley (57) ABSTRACT

Computer systems, computer-implemented methods, and non-transitory computer readable storage media for gross feature recognition including receiving an image comprising a plurality of image elements representing the region of interest of the subject. Gross feature recognition can further include co-registering the image to an atlas to segment the plurality of image elements into a plurality of sub-regions corresponding to structures in the atlas, where the structures (Continued)

in the atlas are ordered in a first rank order according to a predetermined feature. Further included can be ordering the plurality of sub-regions in a second rank order according to the predetermined feature. Further included can be identifying as gross features one or more of the plurality of sub-regions whose positions in the first rank order of the ordered sub-regions differ from positions in the second rank order of the corresponding ordered structures in the atlas.

42 Claims, 5 Drawing Sheets

(51) Int. Cl.

| | | |
|---|---|---|
| A61B 5/055 | (2006.01) | |
| A61B 5/00 | (2006.01) | |
| A61B 6/03 | (2006.01) | |
| A61B 8/00 | (2006.01) | |
| G06T 7/33 | (2017.01) | |
| G06T 7/11 | (2017.01) | |

(52) U.S. Cl.
CPC ............. *A61B 5/055* (2013.01); *A61B 6/032* (2013.01); *A61B 6/037* (2013.01); *A61B 8/00* (2013.01); *G06T 7/11* (2017.01); *G06T 7/337* (2017.01); *A61B 2576/026* (2013.01); *G06T 2207/10081* (2013.01); *G06T 2207/10088* (2013.01); *G06T 2207/10104* (2013.01); *G06T 2207/10132* (2013.01); *G06T 2207/20128* (2013.01); *G06T 2207/30016* (2013.01)

(58) Field of Classification Search
CPC . G06T 2207/10081; G06T 2207/10088; G06T 2207/10104; G06T 2207/10132; G06T 2207/20128; G06T 2207/30016; G06T 2207/30101; A61B 5/0037; A61B 5/0042; A61B 5/055; A61B 6/032; A61B 6/037; A61B 8/00
See application file for complete search history.

(56) References Cited

U.S. PATENT DOCUMENTS

| | | | |
|---|---|---|---|
| 9,563,950 B2* | 2/2017 | Raj | G06K 9/469 |
| 9,607,373 B2* | 3/2017 | Buisseret | G06T 7/0012 |
| 9,734,632 B2* | 8/2017 | Thomas | G06T 19/003 |
| 2005/0215884 A1 | 9/2005 | Greicius et al. | |
| 2008/0154118 A1 | 6/2008 | Dale et al. | |
| 2011/0235884 A1 | 9/2011 | Schreibmann et al. | |
| 2013/0172727 A1 | 7/2013 | Mori et al. | |
| 2015/0366536 A1* | 12/2015 | Courtney | A61B 5/0066 600/427 |
| 2017/0309069 A1* | 10/2017 | Thomas | G06T 19/20 |

FOREIGN PATENT DOCUMENTS

| | | |
|---|---|---|
| WO | 2011/137370 A2 | 11/2011 |
| WO | 2011/163391 A2 | 12/2011 |
| WO | 2012/058217 A2 | 5/2012 |

OTHER PUBLICATIONS

Carballido-Gamio et al., "Longitudinal Analysis of MRI T2 Knee Cartilage Laminar Organization in a Subset of Patients From the Osteoarthritis Initiative: A Texture Approach," Magnetic Resonance in Medicine, 65, pp. 1184-1194 (2011).
Chi et el., "Content-based image retrieval of multiphrase CT images for focal liver lesion characterization," Med. Phys., 40(10): pp. 103502-1-403502-13 (2013).
Collins et al., "Learning Metrics for Content-Based Medical Image Retrieval," 34th Annual International Conference of the IEEE EMBS, Osaka, Japan, pp. 3363-3366 (Jul. 3-7, 2013).
Dube et al., "Content Based Image Retrieval for MR Image Studies of Brain Tumors," Proceedings of the 28th IEEE EMBS Annual International Conference, New York City, USA, pp. 3337-3340 (Aug. 30-Sep. 3, 2006).
Endo et al., "Content-based image-retrieval system—development, usefulness and perspectives of diagnostic assistant robot," Gan To Kagaku Ryoho, 39(7): pp. 1039-1043 (Jul. 2012) (Abstract only).
Huang et al., "Retrieval of Brain Tumors with Region-Specific Bag-of-Visual-Words Representations in Contrast-Enhanced MRI Images," Computational an Mathematical Methods in Medicine, vol. 2012, pp. 1-17.
Kumar et al., "Content-Based Medical Image Retrieval: A Survey of Applications to Multidimensional and Multimodality Data," J. Digit. Imaging, 26: pp. 1025-1039 (2013).
Lu et al., "Fast Video Shot Boundary Detection Based on SVD and Pattern Matching," IEEE Transactions on Image Processing, vol. 22, No. 12, pp. 5136-5145 (Dec. 2013).
Markonis et al., "User Tests for Assessing a Medical Image Retrieval System: A Pilot Study," Medinfo, pp. 224-228 (2013).
Meghdadi et al., "Interactive Exploration of Surveillance Video through Action Shot Summarization and Trajectory Visualization," IEEE Transactions on Visualization and Computer Graphics, vol. 19, No. 12, pp. 2119-2128 (Dec. 2013).
Momennejad et al., "Human anterior prefrontal cortex encodes the 'what' and 'when' of future intentions," NeuroImage, 61, pp. 139-148 (2009).
Muller et al., "A review of content-based image retrieval systems in medical applications—clinical benefits and future directions," International Journal of Medical Informatics, 73, pp. 1-23 (2004).
Puentes et al., "Information quality measurement of medical encoding support based on usability," Computer Methods and Programs in Biomedicine, 112, pp. 329-342 (2013).
Qin et al., "Gross feature recognition of Anatomical Images based on Atlas grid (GAIA): Incorporating the local discrepency between an atlas and a target image to capture the features of anatomic brain MRI," NeuroImage: Clinical. vol. 3, pp. 202-211 (2013).
Reggev et al., "Are all judgments created equal? An fMRI study of semantic and episodic metamemory predictions," Neuropsychologia, 49, pp. 1332-1342 (2011).
Tarjoman et al., "An implementation of a CBIR system based on SVM learning scheme," Journal of Medical Engineering & Technology, 37(1), pp. 43-47 (2013).
Uscumlic et al., "An Iterative Framework for EEG-based Image Search: Robust Retrieval with Weak Classifiers," PLOS One, vol. 8, Issue 8, e72018, pp. 1-8 (Aug. 2013).
Wang et al., "Machine learning and radiology," Medical Image Analysis, 16, pp. 933-951 (2012).
Xia et al., "Online Multiple Kemal Similarity Learning for Visual Search," IEEE Transactions on Pattern Analysis and Machine Intelligence, vol. 36, No. 3, pp. 536-549 (Mar. 2014).
Yang et al., "Content-based retrieval of brain tumor in contrast-enhanced MRI images using tumor margin information and learned distance metric," Med. Phys., 39(11), pp. 6929-6942 (Nov. 2012).
Zhang et al., "Content-based automatic retinal image recognition and retrieval system," Journal of Biomedical Engineering, 30(2): pp. 403-408 (Apr. 20113) (Abstract Only).

\* cited by examiner

GROSS FEATURE RECOGNITION OF ANATOMICAL IMAGES BASED ON ATLAS GRID

CROSS REFERENCE TO RELATED APPLICATIONS

This is a national stage application under 35 U.S.C. § 371 of PCT/US2014/069158 filed Dec. 8, 2014, which claims the benefit of U.S. Provisional Patent Application No. 61/913,146, filed Dec. 6, 2013, which is hereby incorporated by reference herein in its entirety.

STATEMENT OF GOVERNMENT SUPPORT

This invention was made with government support under AG005146, AG020012, AG033774, RO1DC011317, R21AG033774, RO1HD065955, K24DA61427, U54NS56883, P41EB015909, U24RR021382, P01EB00195, RO1AG20012, K23EY015802, R21NS059830, MO1RR000052, R01N5056307, RC1NS068897, and P50AG005146 awarded by the National Institutes of Health, and under G12-RR003061 awarded by the National Center for Research Resources. The government has certain rights in the invention.

TECHNICAL FIELD

This disclosure relates generally to gross feature recognition of anatomical images and more particularly to methods, system, and media for gross feature recognition of anatomical images.

BACKGROUND

Existing transformation-based image analysis uses direct anatomical information, such as shape, volume, and intensity of anatomical structures. These methods use image contrast to guide the transformation, and therefore, are sensitive to the variation in contrast not only due to the anatomical abnormalities, but also to the differences in scanner and image parameters.

Conventional structural MRI still plays a leading part in clinical diagnostic radiology, providing vast amounts of anatomical information. There are numerous clinical hallmarks and signs that can be depicted by structural MRI, which are well established after more than 30 years of clinical application. Currently, clinical MR images are interpreted by radiologists and stored electronically in the picture archiving and communication system (PACS) with the radiology reports. A text-based image searching of PACS enables the retrieval of stored images with the clinical information and radiology report. This searching capability dramatically improved daily clinical practice by saving time and effort to collect images from a patient to evaluate disease progression and the efficacy of treatments, and to collect images from a specific clinical condition to investigate the common anatomical phenotype depicted by MRI.

However, to further aid in clinical use, an image-based search, in which the patient's image is submitted to PACS as a "keyword," and past images with similar anatomical phenotypes are identified, and a statistical report about the diagnosis and prognosis is provided, would be far more informative. This type of image searching is called content-based image retrieval (CBIR), which is an anticipated technology in medical imaging (El-Kwae et al., 2000; Greenspan and Pinhas, 2007; Muller et al., 2005; Orphanoudakis et al., 1996; Rahman et al., 2007; Robinson et al., 1996; Sinha et al., 2001; Unay et al., 2010). Although the CBIR is a promising technology, to date, the application to PACS is limited (Muller et al., 2004; Sinha and Kangarloo, 2002), because of the difficulty of extracting features from the stored images, especially for brain MRI, which consists of numerous anatomical structures with highly varying intensity, volume, and shape among diseases and even among normal individuals.

One of the solutions is to apply image quantification technologies, which has been the subject of extensive research in the last two decades (Ashburner and Friston, 1999; Chiang et al., 2008; Good et al., 2001; Mazziotta et al., 2001; Smith et al., 2006; Verma et al., 2005; Wright et al., 1995; Yushkevich et al., 2008; Zhang et al., 2006). These analyses have been mostly designed for traditional group-based studies, in which strict inclusion criteria and age-matched controls were essential, but often incompatible, with clinical practice where an individual image, not a group of diseases, is the target of the analysis.

The concept of group analysis assumes consistent locations of abnormalities, which does not hold for clinical situations with heterogeneous patient populations and image quality. There are diseases with lesions that are not seen in the normal brain, such as stroke and brain tumors, and diseases with atrophy in a specific set of anatomical structures, such as Alzheimer's disease. To localize the disease-related pathological changes seen in brain MRI, transformation-based image analysis methods are often employed. However, the lesions with abnormal intensity or the space-occupying lesions often cause significant misregistration of brain structures after image transformation.

The brain with severe atrophy, such as that seen in Alzheimer's disease, is also problematic in terms of the transformation accuracy. There are methods to overcome such inaccuracy by using specific approaches, such as lesion-masking (Andersen et al., 2010; Ripolles et al., 2012) or a disease-specific template (Liao et al., 2012; Mandal et al., 2012; Wang et al., 2012) (e.g., http://www.loni.ucla.edu/Atlases/), but it is still difficult to quantify various types of diseases in the same methodological framework. In addition, most of these methods use image contrast to guide the transformation, and therefore, are sensitive to the variation in contrast not only due to the anatomical abnormalities, but also to the differences in scanner and image parameters.

What is needed are methods, system, and media that are robust to this inhomogeneity seen in clinical images, and that use information about a structural misregistration and intensity mismatch after image registration to capture the anatomical features, instead of direct anatomical information.

SUMMARY

Various embodiments are generally directed to gross feature recognition of anatomical images to overcome the aforementioned problems.

In one aspect of the invention, a computer-implemented method for recognizing gross features from a region of interest of a subject includes: receiving an image comprising a plurality of image elements representing the region of interest of the subject to a data storage device; co-registering, using at least one data processor, the image to an atlas to segment the plurality of image elements into a plurality of sub-regions corresponding to structures in the atlas, wherein the structures in the atlas are ordered in a first rank order according to a predetermined feature of the structures;

ordering, using the at least one data processor, the plurality of sub-regions in a second rank order according to the predetermined feature; and identifying as gross features one or more of the plurality of sub-regions whose positions in the second rank order of the ordered sub-regions differ from positions in the first rank order of the corresponding ordered structures in the atlas.

In another aspect of the invention, a computer-implemented method for searching an image database for one or more result images comprising gross features in a region of interest, includes receiving an image having a plurality of image elements representing the region of interest of a subject to a data storage device; co-registering, using at least one data processor, the image to an atlas to segment the plurality of image elements into a plurality of sub-regions corresponding to structures in the atlas, where the structures in the atlas are ordered in a first rank order according to a predetermined feature of the structures; ordering the plurality of sub-regions in a second rank order, using at least one data processor, according to the predetermined feature; and identifying one or more result images from the image database that have a substantially same rank order for the region of interest as the second rank order of the plurality of sub-regions according to the predetermined feature.

In another aspect of the invention, a computer system for recognizing gross features from a region of interest of a subject, includes a memory storing computer-executable instructions; and at least one data processor that is coupled to the memory and that is configured to execute the computer-executable instructions to: 1) receive an image comprising a plurality of image elements representing the region of interest of the subject; 2) co-register the image to an atlas to segment the plurality of image elements into a plurality of sub-regions corresponding to structures in the atlas, where the structures in the atlas are ordered in a first rank order according to a predetermined feature of the structures; 3) order the plurality of sub-regions in a second rank order according to the predetermined feature; and 4) identify as gross features one or more of the plurality of sub-regions whose positions in the first rank order of the ordered sub-regions differ from positions in the second rank order of the corresponding ordered structures in the atlas.

In another aspect of the invention, a non-transitory computer readable storage medium for recognizing gross features from a region of interest of a subject includes instructions that when executed enables a computing system to: receive an image comprising a plurality of image elements representing the region of interest of the subject; co-register the image to an atlas to segment the plurality of image elements into a plurality of sub-regions corresponding to structures in the atlas, wherein the structures in the atlas are ordered in a first rank order according to a predetermined feature; order the plurality of sub-regions in a second rank order according to the predetermined feature; and identify as gross features one or more of the plurality of sub-regions whose positions in the first rank order of the ordered sub-regions differ from positions in the second rank order of the corresponding ordered structures in the atlas.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

Embodiments will now be described in connection with the associated drawings, in which.

DETAILED DESCRIPTION OF THE DRAWINGS

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference herein in their entireties as if each had been individually incorporated.

The term "computer" is intended to have a broad meaning that may be used in computing devices such as, e.g., but not limited to, standalone or client or server devices. The computer may be, e.g., (but not limited to) a personal computer (PC) system running an operating system such as, e.g., (but not limited to) MICROSOFT® WINDOWS® NT/98/2000/XP/Vista/Windows 7/8/etc. available from MICROSOFT® Corporation of Redmond, Wash., U.S.A. or an Apple computer executing MAC® OS from Apple® of Cupertino, Calif., U.S.A. However, the invention is not limited to these platforms. Instead, the invention may be implemented on any appropriate computer system running any appropriate operating system. In one illustrative embodiment, the present invention may be implemented on a computer system operating as discussed herein. The computer system may include, e.g., but is not limited to, a main memory, random access memory (RAM), and a secondary memory, etc. Main memory, random access memory (RAM), and a secondary memory, etc., may be a computer-readable medium (e.g., a non-transitory computer readable storage medium) that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The secondary memory may include, for example, (but is not limited to) a hard disk drive and/or a removable storage drive, representing a floppy diskette drive, a magnetic tape drive, an optical disk drive, a compact disk drive CD-ROM, flash memory, etc. The removable storage drive may, e.g., but is not limited to, read from and/or write to a removable storage unit in a well-known manner. The removable storage unit, also called a program storage device or a computer program product, may represent, e.g., but is not limited to, a floppy disk, magnetic tape, optical disk, compact disk, etc. which may be read from and written to the removable storage drive. As will be appreciated, the removable storage unit may include a computer usable storage medium having stored therein computer software and/or data.

In alternative illustrative embodiments, the secondary memory may include other similar devices for allowing computer programs or other instructions to be loaded into the computer system. Such devices may include, for example, a removable storage unit and an interface. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units and interfaces, which may allow software and data to be transferred from the removable storage unit to the computer system.

The computer may also include an input device may include any mechanism or combination of mechanisms that may permit information to be input into the computer system from, e.g., a user. The input device may include logic configured to receive information for the computer system from, e.g. a user. Examples of the input device may include, e.g., but not limited to, a mouse, pen-based pointing device, or other pointing device such as a digitizer, a touch sensitive display device, and/or a keyboard or other data entry device (none of which are labeled). Other input devices may include, e.g., but not limited to, a biometric input device, a video source, an audio source, a microphone, a web cam, a video camera, and/or other camera. The input device may communicate with a processor either wired or wirelessly.

The computer may also include output devices which may include any mechanism or combination of mechanisms that may output information from a computer system. An output device may include logic configured to output information from the computer system. Embodiments of output device may include, e.g., but not limited to, display, and display interface, including displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. The computer may include input/output (I/O) devices such as, e.g., (but not limited to) communications interface, cable and communications path, etc. These devices may include, e.g., but are not limited to, a network interface card, and/or modems. The output device may communicate with processor either wired or wirelessly. A communications interface may allow software and data to be transferred between the computer system and external devices.

The term "data processor" is intended to have a broad meaning that includes one or more processors, such as, e.g., but not limited to, that are connected to a communication infrastructure (e.g., but not limited to, a communications bus, cross-over bar, interconnect, or network, etc.). The term data processor may include any type of processor, microprocessor and/or processing logic that may interpret and execute instructions (e.g., for example, a field programmable gate array (FPGA)). The data processor may comprise a single device (e.g., for example, a single core) and/or a group of devices (e.g., multi-core). The data processor may include logic configured to execute computer-executable instructions configured to implement one or more embodiments. The instructions may reside in main memory or secondary memory. The data processor may also include multiple independent cores, such as a dual-core processor or a multi-core processor. The data processors may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

The term "data storage device" is intended to have a broad meaning that includes removable storage drive, a hard disk installed in hard disk drive, flash memories, removable discs, non-removable discs, etc. In addition, it should be noted that various electromagnetic radiation, such as wireless communication, electrical communication carried over an electrically conductive wire (e.g., but not limited to twisted pair, CAT5, etc.) or an optical medium (e.g., but not limited to, optical fiber) and the like may be encoded to carry computer-executable instructions and/or computer data that embodiments of the invention on e.g., a communication network. These computer program products may provide software to the computer system. It should be noted that a computer-readable medium that comprises computer-executable instructions for execution in a processor may be configured to store various embodiments of the present invention.

This disclosure describes a novel way to extract features of medical images. To overcome the wide range of anatomical variability in clinical cases and the inconsistency of imaging protocols, we introduced the Gross feature recognition of Anatomical Images based on Atlas grid (GAIA), in which the local intensity alteration, caused by pathological or physiological (development and aging) intensity changes, as well as by atlas-image misregistration, is used to capture the anatomical features of target images. A novelty of the GAIA is the use of anatomical parcellation maps to measure the degree of misregistration and structural intensity mismatch, which have been regarded as errors to be excluded in traditional transformation-based image analysis. After the overall shape and size of the target image are roughly adjusted to that of the atlas using low-elasticity transformation, there are residual misregistrations in most anatomical areas. The anatomical parcellation map is used to measure intensity of each parcel, which represents a combination of the atlas-image segmentation and intensity disagreements. This could be used to capture the anatomical features specific to the target image.

Figure 1:
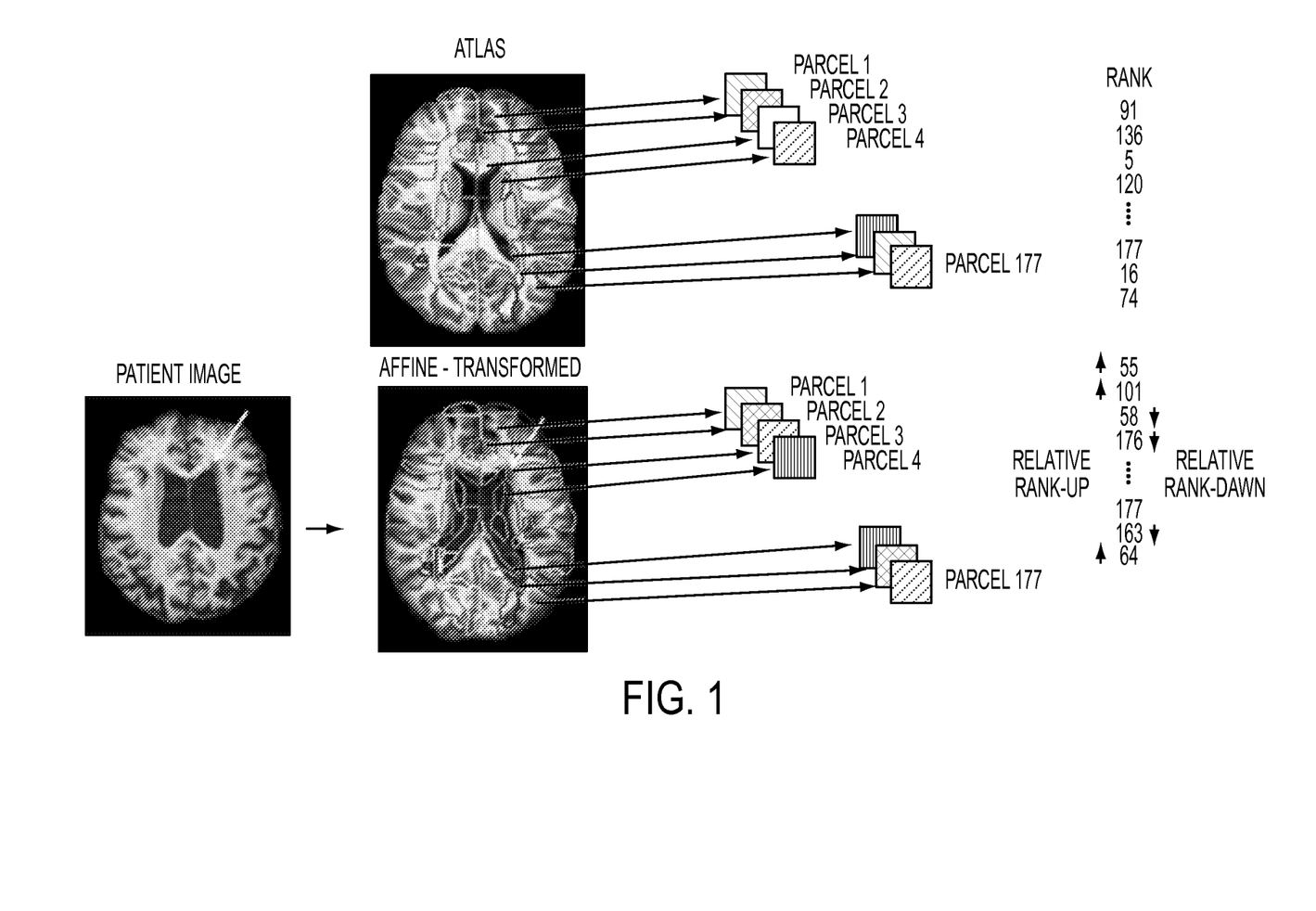
FIG. 1 depicts an exemplary GAIA Procedure in accordance with one or more embodiments.

In one embodiment, we attempt to solve this widely known problem in transformation-based analysis by introducing an approach named the "Gross feature recognition of Anatomical Images based on Atlas grid (GAIA)," for image feature extraction (FIG. 1). In one embodiment of GAIA, images are co-registered to the atlas using linear transformation, followed by intensity measurement for the multiple areas in the atlas space. The overall shape and size can be only roughly adjusted to that of the atlas, leaving residual misregistrations in most of the anatomical areas. The measured intensity of each area represents a combination of the local intensity alteration, caused by pathological (e.g., ischemia) or physiological (development and aging) intensity changes, as well as by atlas-image misregistration, which are recorded as unique anatomical features in a quantitative standardized matrix. Since the goal of CBIR is to retrieve images based on anatomical similarity, an interest is not necessarily how accurately images can be warped, but how to extract imaging features that can separate a specific diagnostic group from other conditions. This motivated us to use the GAIA as a method for the image recognition applied to a pool of clinical MRIs with a mixture of various diseases.

In FIG. 1, a computer-implemented method, computer system and/or non-transitory computer readable storage medium for recognizing gross features from a region of interest of a subject is shown. The method of FIG. 1 can include receiving an image 104 having a plurality of image elements representing the region of interest of the subject. In one embodiment, the image 104 can be generated from at least one of magnetic resonance imaging (MRI), computed tomography (CT), positron emission tomography (PET), ultrasound, or nuclear tracer three-dimensional imaging. The method can also include co-registering the image to an atlas 106 to segment the plurality of image elements into a plurality of sub-regions corresponding to structures in the atlas. The structures in the atlas 106 can be ordered, for example in a first rank order 110, according to a predetermined feature of the structures. The method can further include ordering the plurality of sub-regions, for example in a second rank order 112, according to the predetermined feature. The method can include identifying as gross features one or more of the plurality of sub-regions whose positions in the second rank order 112 of the ordered sub-regions differ from positions of the first rank order 110 of the corresponding ordered structures in the atlas. In one embodiment, the plurality of image elements are pixels or voxels.

In one embodiment, the gross features can be sub-regions whose positions in the second rank order of ordered sub-regions differ from the positions in the first rank order of the corresponding structures in the atlas by a statistically significant number of positions. In one embodiment, the gross features can be sub-regions whose positions in the second rank order differ from the positions in the first rank order of the corresponding structures in the atlas by at least three positions. A rank order can be an ordered representation or set that indicates the rank of each of the sub-regions, parcels, or structures in the atlas as it relates to all the sub-regions, parcels, or structures, respectively.

In one embodiment, the predetermined feature can be a measure of intensity. For example, FIG. 1 depicts a GAIA Procedure in which all images are co-registered to the atlas space using affine transformation. In other embodiments, the images can be co-registered to the atlas using a linear and/or a non-linear transformation. The atlas segmentation map (colored contour) is overlaid on the co-registered image. The mean intensity of each of 177 parcels is calculated and ranked by the order of mean intensity. Namely, the area with highest intensity is ranked #1 and the area with lowest intensity is ranked #177. Note that the intensity includes information about both misregistration and intensity mismatch between the atlas and the target image. For example, parcels with cerebrospinal fluid contamination (e.g., parcel 4) and with low intensity change, such as the periventricular cap (yellow arrows, parcel 3), were ranked lower than that of the atlas.

In one embodiment, the measure of intensity can be a mean intensity of the image elements in the sub-region of the co-registered image. In another embodiment, the measure of intensity can be a sum of intensities of the image elements in the sub-region. In another embodiment, the measure of intensity can be a highest intensity of the image elements in the sub-region. In another embodiment, the measure of intensity can be a lowest intensity of the image elements in the sub-region.

Texture of each sub-region can also be extracted as the feature of the extracted image. For example, various texture parameters can be used such as histogram, absolute gradient, run-length matrix, co-occurrence matrix, auto-regressive model, and wavelets. Additionally, various scalar values can also be extracted from these parameters and applied in the ordering. For example, kurtosis and skewness can be extracted from the histogram. Measure of intensity and texture can also be extracted together as features of the images.

In one embodiment, the image can be co-registered to the atlas using a linear and/or nonlinear transformation. In one embodiment, the plurality of image elements are pixels or voxels. In one embodiment, the region of interest of the subject can include a portion of at least a brain, a heart, a liver, skin, another organ, one or more bones, or any combination thereof.

In one embodiment, the method can further include creating a feature vector storing identifiers of the ordered plurality of sub-regions, where placement in the feature vector indicates the position of the sub-regions in the second rank order.

In another embodiment, the method can further include identifying a second feature vector whose correlation with the feature vector exceeds a threshold. In this embodiment, the second feature vector can be associated with the region of interest of another subject and an anatomical feature of the other subject. The method can also include providing a likelihood that the subject has the anatomical feature. In some embodiments, the anatomical feature can be at least one of an abnormality, a disease, a condition, a diagnosis, or any combination thereof.

In another embodiment, a computer-implemented method, computer system and/or non-transitory computer readable storage medium can be used for searching an image database for one or more result images having gross features in a region of interest. In this embodiment, the method can include receiving an image 104 having a plurality of image elements representing the region of interest of a subject. In one embodiment, the image 104 can be generated from at least one of magnetic resonance imaging (MRI), computed tomography (CT), positron emission tomography (PET), ultrasound, or nuclear tracer three-dimensional imaging. The method can include co-registering the image 104 to an atlas 106 to segment the plurality of image elements into a plurality of sub-regions or parcels (e.g., 1-177) corresponding to structures in the atlas. The structures in the atlas can be ordered in a first rank order 110 according to a predetermined feature of the structures. The method can include ordering the plurality of sub-regions in a second rank order 112 according to the predetermined feature. The method can include identifying one or more result images from the image database that have a substantially same rank order for the region of interest as the second rank order 112 of the plurality of sub-regions according to the predetermined feature.

In one embodiment, the identifying step in the method for searching an image database for one or more result images can include the one or more result images being identified from the image database by comparing a feature vector representing the ordering of the plurality of sub-regions with feature vectors of the images representing the orderings of sub-regions of the images.

In another embodiment, the method for searching an image database can further include providing a likelihood that the subject has an anatomical feature associated with the one or more result images. The anatomical feature of the method can include an abnormality, a disease, a condition, a diagnosis or any combination thereof.

In one embodiment, the gross features can be image intensities of the sub-regions, which may be normalized to enhance cross-patient feature comparison.

2. Methods 2.1 Participants and Image Acquisitions

A de-identified database consisting of T1-weighted images scanned with a magnetization-prepared rapid gradient recalled echo (MPRAGE) sequence, collected through four independent clinical research studies (Faria et al., 2013; Jung et al., 2012; Oishi et al., 2011; Unschuld et al., 2012), was analyzed retrospectively. The Institutional Review Board approved each study, and written, informed consent was obtained.

2.1.1 AD, mild cognitive impairment (MCI), and the cognitively normal (NC) control group: Twenty five probable-AD patients who met NINCDS/ADRDA criteria (McKhann et al., 1984), with a clinical dementia rating (CDR) of 1; 25 aMCI patients who met the criteria for amnestic MCI (Petersen, 2004) with a CDR=0.5; and 25 NC participants with a CDR=0, were included. There were no differences among these groups with regard to age, race, education, and the occurrence of vascular conditions (Mielke et al., 2009). After three years of follow-up, six MCI patients had converted to AD and were defined as MCI converters (MCI_c); three NC participants had converted to AD and were defined as NC converters (NC_c). The diagnosis and neuropsychiatric evaluations [CDR, the Alzheimer's Disease Assessment Scale-cognitive portion (ADAS-cog), the mini mental state examination (MMSE), and the geriatric depression scale (GDS)] were performed at the time of the MRI scan.

MPRAGE sequences were acquired using a 3T scanner (Gyroscan NT, Philips Medical Systems) located in the Kennedy Krieger Institute. The scan parameters were: repetition time (TR) 6.9 ms; echo time (TE) 3.2 ms; inversion time (TI) 846.3 ms; matrix 256×256×170; field of view (FOV) 240 mm×240 mm×204 mm, zero-filled to 256 mm×256 mm×204 mm (protocol-1).

2.1.2 HD and the control group: Sixty-four participants positive for CAG expansion in Huntingtin and twenty-seven control subjects negative for CAG expansion were included. Among those positive for CAG expansion, thirteen participants were early symptomatic (HD_es) and 51 participants were asymptomatic, including 22 who were close to onset (HD_cto; less than 10 years to the estimated onset of the motor symptom) and 19 who were far from onset (HD_ffo; more than or equal to 10 years to the estimated onset of the motor symptom), based on the CAG-repeat length of the mutated Huntingtin allele and age (Langbehn et al., 2004). Disease burden score (DBS) was calculated as ([CAG-repeat length−35.5]×age) (Penney et al., 1997). The Montreal Cognitive Assessment (MoCA) was performed to screen for mild cognitive dysfunction on the day of scanning. None of the participants had a history of diagnosed mood, obsessive compulsive, or psychotic disorder or substance abuse.

MPRAGE were acquired using a 3T scanner (Intera, Philips Medical Systems) located in the Kennedy Krieger Institute. Two different protocols were used, including protocol-2: TR 8.4 ms; TE 3.8 ms; TI 826 ms; matrix 256×256×150; FOV230 mm×230 mm×135 mm, zero-filled to 256 mm×256 mm×135 mm; Flip angle=8 degree; and protocol-3: TR 8.0 ms; TE 3.7 ms; TI 811 ms; matrix 256×256×150; FOV 256 mm×256 mm×150 mm.

2.1.3 SCA6 group and the control group: Twenty-four patients with genetically diagnosed SCA6 and eight controls were enrolled. The duration of disease was defined from the first self-reported symptom of ataxia. The Scale for the Assessment and Rating of Ataxia (SARA) was performed for the evaluation of ataxic symptoms.

MPRAGE sequences were acquired using a 3T scanner (Intera, Philips Medical Systems) located in the Kennedy Krieger Institute. The scan parameters were: TR 10.33 ms; TE 6.0 ms; TI 964.8 ms; matrix 256×256×140; FOV 212 mm×212 mm×151 mm, zero-filled to 256 mm×256 mm×151 mm (protocol-4).

2.1.4 PPA group: Fifty seven participants with PPA, diagnosed on the basis of having a predominant and progressive deterioration in language in the absence of major change in personality, behavior, or cognition other than praxis for at least two years (Mesulam, 1982), and, a control group without neurological symptoms, were included. PPA patients were classified as one of the variants of PPA according to recent guidelines (Gorno-Tempini et al., 2011), including non-fluent variant (PPA_NFv), semantic variant (PPA_Sv), and logopenic variant (PPA_Lv). Participants with only anomia and dysgraphia, and who did not meet the criteria for any of these variants, were categorized as unclassified PPA (PPA_U). All participants completed the Western Aphasia Battery (WAB) (Shewan and Kertesz, 1980) within one month before the MRI scans.

MPRAGE sequences were acquired using two 3T scanners. The one located in the Kennedy Krieger Institute (Achieva, Philips Medical Systems) was used for protocol-5: TR 8.4 ms; TE 3.9 ms; TI 849.4 ms; matrix 256×256×140; FOV 212 mm×212 mm×140 mm, zero-filled to 256 mm×256 mm×154 mm. The other located in the Johns Hopkins Hospital (Achieva, Philips Medical Systems) was used for protocol-6: TR 6.6 ms; TE 3.1 ms; TI 821 ms; matrix 256×256×120; FOV 230 mm×230 mm×120 mm, zero-filled to 256 mm×256 mm×120 mm.

The MRIs from AD, HD_es, SCA6, PPA_Sv, PPA_NFv, PPA_Lv, PPA_U, and the control groups of each study were pseudo-randomly assigned to either training or test datasets. MRIs from NC_c, MCI, MCI_c, HD_cto, and HD_ffo were assigned as a test dataset.

2.2 Image Processing

All images were re-sliced to 1 mm isotropic resolution (181×217×181 matrix), bias corrected, and skull-stripped to generate the "prepared" images by using SPM8 (http://www.fil.ion.ucl.ac.uk/spm/). The intensity histogram peaks of the cerebrospinal fluid (CSF), the gray matter (GM), and the white matter (WM) of the "prepared" images were adjusted to match that of the JHU-MNI atlas (http://cmrm.med.jhmi.edu/) using a nonlinear histogram matching routine implemented in DiffeoMap (www.mristudio.org). After intensity correction, 12-parameter affine transformation of AIR (Woods et al., 1998), implemented in DiffeoMap, was applied to the prepared images to co-register each participant's image to the atlas. The parcellation map of the JHU-MNI atlas was overlaid on the co-registered images to measure the mean intensity of the 177 areas. The measured intensity was converted to the rank order using the standard competition ranking. Namely, a structure with the highest intensity was ranked #1 and the lowest intensity was ranked #177. This conversion was performed to ameliorate the differences in intensity profile among different scan protocols, which might remain even after the bias and intensity corrections.

The novelty of the GAIA is the use of parcellation maps to measure the degree of misregistration and structural intensity mismatch, which have been regarded as errors to be excluded in traditional transformation-based image analysis. Although the overall shape and size are roughly adjusted to that of the atlas after affine transformation, there are residual misregistrations in most anatomical areas (FIG. 1). For example, if a given image has an enlargement in the lateral ventricle, the area defined as the caudate in the atlas is occupied by the enlarged ventricle, which results in lower intensity in this area because of the contamination of the cerebrospinal fluid (parcel 4 of FIG. 1), and hence, this results in a relative lowering of the rank order in this parcel (rightmost column of FIG. 1). If the image contains lesions with altered intensity, such as the periventricular cap, this also lowers the intensity of the corresponding area (parcel 3 of FIG. 1), which also results in a relative lowering of the rank order in this parcel. Our hypothesis is that the rank order, which represents a combination of the atlas-image segmentation and intensity disagreements, could be used to capture the anatomical features specific to the target image.

2.3 Normalization of the Ranking

Training dataset: The rank ($Rtrain_{ij}$) of image i, area j was further converted to a z-score: $Ztrain_{ij}=(Rtrain_{ij}-\overline{RN}_{Cj})/\sigma N_{Cj}$, where $\overline{RN}_{Cj}$ represents the mean rank and $\sigma N_{Cj}$ represents the standard deviation of the area j of normal control images assigned to the training dataset. This resulted in a 102 (number of training data)×177 (number of areas) matrix with $Ztrain_{ij}$ in each element. A portion of this matrix including only normal control images (40×177 matrix) was also created to investigate the effects of age and gender.

Test dataset: The rank ($Rtest_{kj}$) of image k, area j was further converted to a z-score: $Ztest_{kj}=(Rtest_{kj}-\overline{RN}_{Cj})/\sigma N_{Cj}$. This resulted in a 170 (number of test data)×177 matrix with $Ztest_{kj}$ in each element.

2.4 Extraction of Age- and Gender-Related Features Using a Control Subset of the Training Dataset PCA was applied to the 40×177 matrix of $Ztrain_{ij}$ to investigate correlations between extracted principal components (PCs) and age or gender. If significant correlations were identified, the PCA-derived eigenvectors were applied to the 102×177 matrix of $Ztrain_{ij}$ and the 170×177 matrix of $Ztest_{kj}$, from which the PCs with significant correlations were removed. This resulted in $Ztrain_{il}$ and $Ztest_{kl}$, in which l ranges from 1 to m, which is the number of PCs without significant effects of age and gender. Spearman's rank correlation coefficient was applied for the evaluation, in which a corrected p<0.05 (false discovery rate) was considered a significant correlation.

2.5 Extraction of Disease-Specific Features Using a Training Dataset

PCA was applied to the 102×177 matrix of $Ztrain_{ij}$ to extract PCs that could explain >95% of the total variance. Subsequently, LDA was applied to the PCs to extract typical appearances for specific disease categories. The eight statuses (NC, AD, HD_es, SCA6, PPA_Sv, PPA_NFv, PPA_Lv, and PPA_U) were used to label the training dataset. If significant effects of age or gender existed, LDA was also applied to the 102×m matrix of $Ztrain_{il}$. These procedures resulted in eight feature vectors that represented disease-specific anatomical features extracted from the training dataset.

2.6 Evaluation of GAIA Using the Test Dataset

The eight feature vectors derived from the training dataset were applied to the test dataset (the 170×177 matrix of $Ztest_{kj}$ and the 170×m matrix of $Ztest_{kl}$) to calculate the discriminant scores of 13 statuses (NC, NC_c, AD, MCI, MCI_c, HD_es, HD_cto, HD_ffo, SCA6, PPA_Sv, PPA_NFv, PPA_Lv, and PPA_U) for each participant. A one-way analysis of variance was used to test the differences in the 13 statuses, and to test the differences in NC scores from five different scan protocols (protocols 1-5 in Table 1). The group differences in the discriminant scores were assessed using independent-sample t tests, in which p<0.05 was considered significant. Receiver operating characteristic (ROC) curve analysis was performed to assess the classification of each disease group using discriminant scores. The correlations of discriminant scores with clinical scores were analyzed by using the Spearman's rank correlation tests, in which p<0.05 was considered significant. Statistical analyses were performed on SPSS 18/20 (IBM Corp., NY, USA).

3. Results 3.1 Effects of Age, Gender, and Scan Parameters

Figure 2:
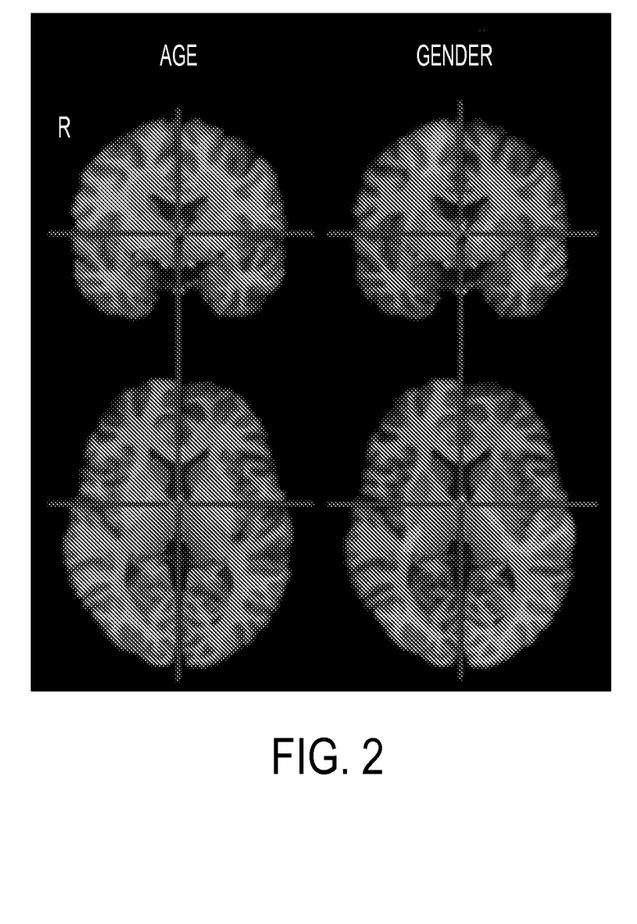
FIG. 2 depicts effects of age and gender on the T1-weighted image in accordance with one or more embodiments.

Thirty-nine PCs were extracted from the 40×177 matrix of $Ztrain_{ij}$. Significant correlations were identified between the first PC and age (Spearman's rho=0.73, $p=8.9\times10^{-8}$), and the 16th PC and gender (Spearman's rho=0.39, $p=1.2\times10^{-2}$) (FIG. 2). Therefore, we created $Ztrain_{il}$ and $Ztest_{kl}$ (l: 1, 2, ..., 37) in which the first and 16th PC were removed. With the effect of age and gender, the NC scores significantly differed among protocols 1-5, with the F (4, 35)=3.648 and $p=1.4\times10^{-2}$. After removing the effects of age and gender, there was no significant difference in the NC scores among protocols 1-5 (F (4, 35)=1.217 and $p=3.2\times10^{-1}$).

FIG. 2 depicts effects of age and gender on the T1-weighted image. The effects of age and gender are color-coded on the 177 areas of the atlas space. The red represents positively weighted areas and the blue represents negatively weighted areas. Weights are relative, and have no applicable units. The images are in radiological convention (R represents the right side). The effect of age is mostly identified around the ventricles. The effect of female gender was found in the left superior temporal, bilateral middle occipital, bilateral subgenual anterior cingulate, and the right prefrontal areas, which were positively weighted, and the left inferior temporal, left precentral, and bilateral superior parietal areas, which were negatively weighted.

3.2 Extraction of Disease-Specific Features

From the $Ztrain_{ij}$ derived from the training dataset, PCA extracted 54 PCs that could explain >95% of the total variance. LDA was applied to the 54 PCs to extract eight feature vectors that could calculate discriminant scores for seven disease statuses and for normal status (FIG. 3A). PCA and subsequent LDA were also applied to the $Ztrain_{il}$ to extract feature vectors without the effects of age and gender (FIG. 3B).

Figure 3:
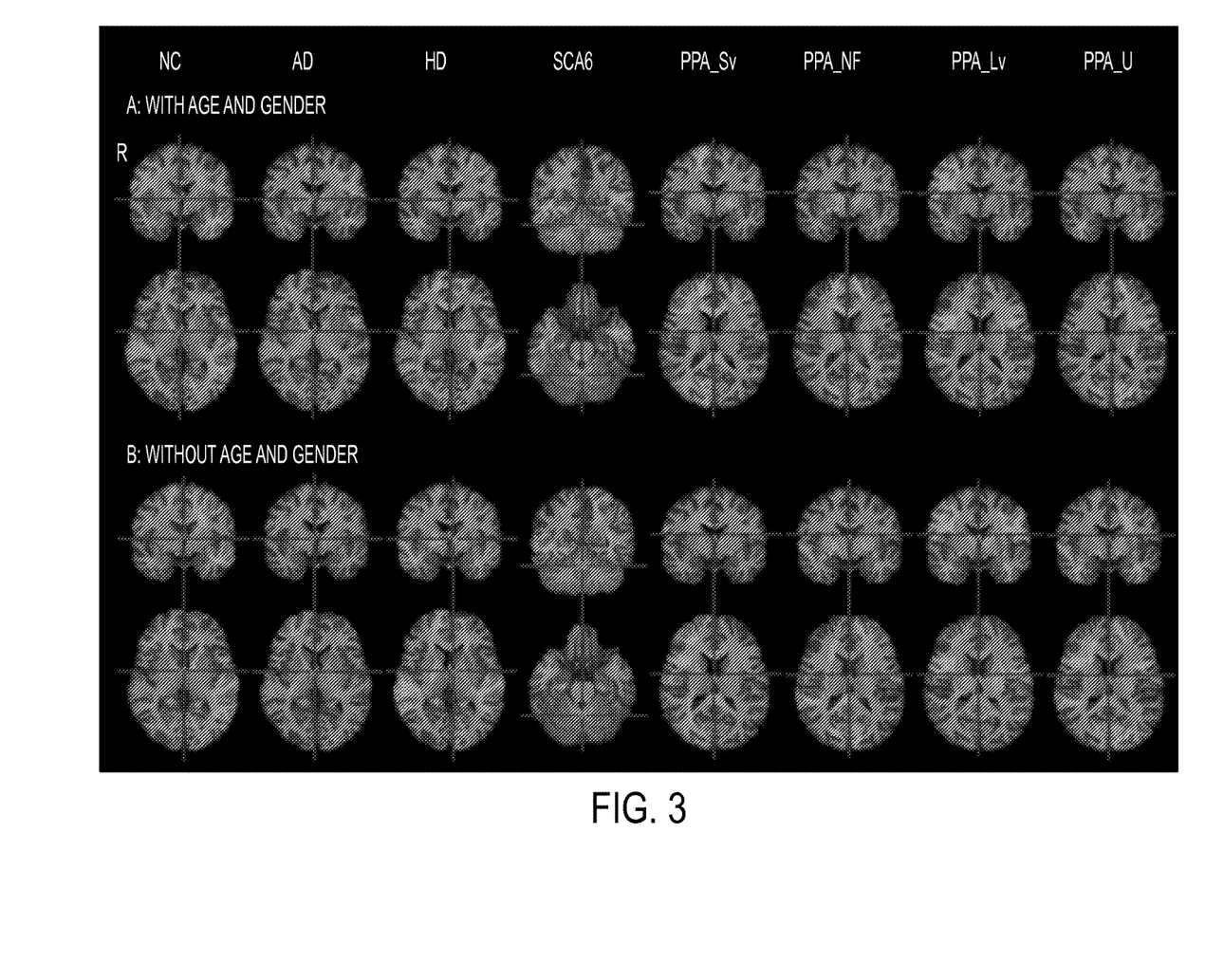
FIG. 3 depicts color-coded feature vectors of eight clinical statuses.

FIG. 3 depicts color-coded feature vectors of eight clinical statuses. The feature vectors are color-coded on the 177 areas of the atlas space. The red represents positively weighted areas and the blue represents negatively weighted areas. Weights are relative, and have no applicable units. The images are in radiological convention (R represents the right side).

3.3 Evaluation of GAIA Using the Test Dataset

Discriminant scores of eight clinical statuses were calculated based on the trained feature vectors. Note that a higher discriminant score represents a closer match to the typical disease-related feature.

Figure 4:
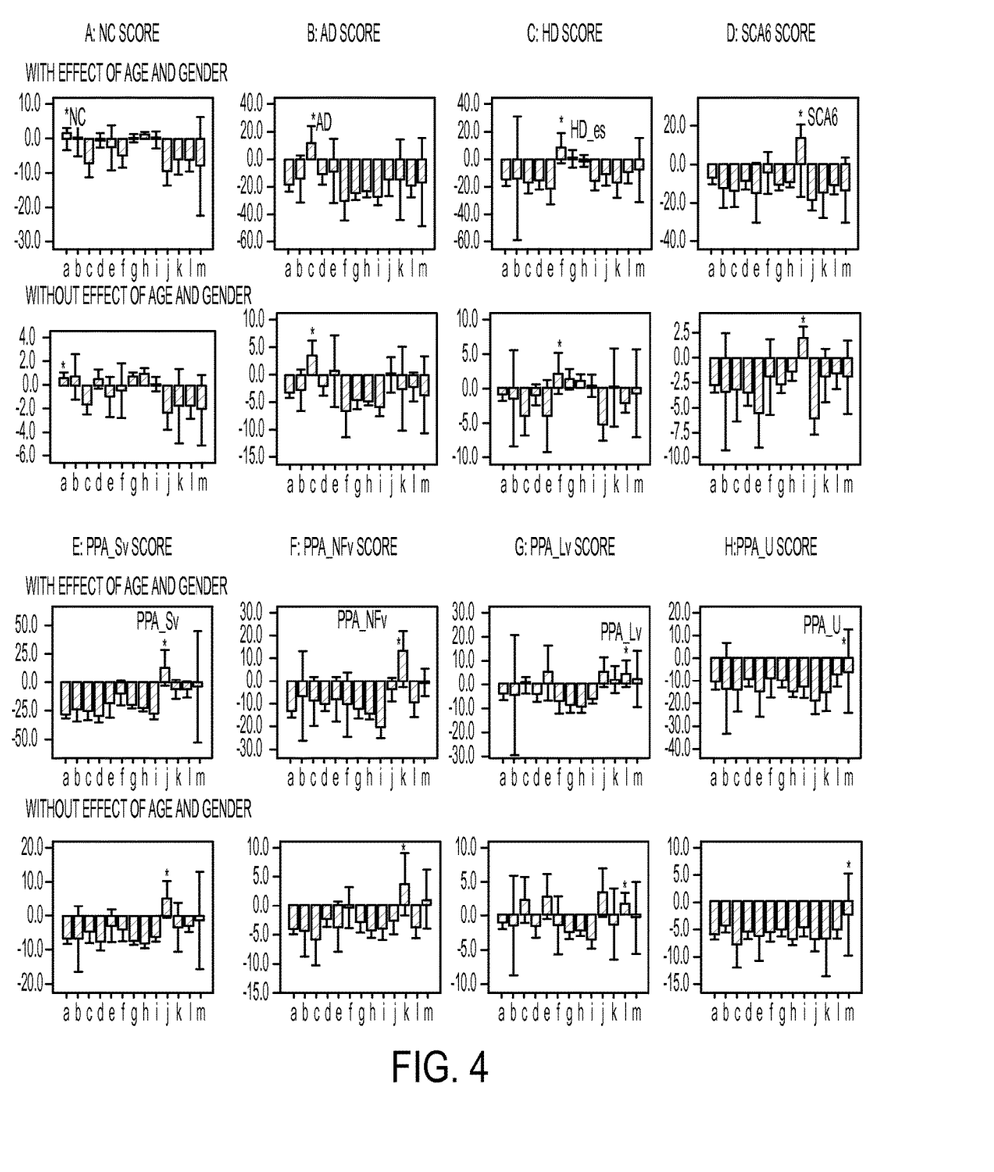
FIG. 4 depicts bar charts of eight discriminant scores from thirteen statuses, with effects of age and gender (upper chart) and without effects of age and gender (lower chart).

FIG. 4 depicts bar charts of eight discriminant scores (A: NC score, B: AD score, C: HD score, D: SCA6 score, E: PPA_Sv score, F: PPA_NFv score, G: PPA_Lv score, and H: PPA_U score) from thirteen statuses (from left to right a: NC, b: NC_c, c: AD, d: MCI, e: MCI_c, f: HD_es, g: HD_cto, h: HD_ffo, is SCA6, j: PPA_Sv, k: PPA_NFv, l: PPA_Lv, and m: PPA_U), with effects of age and gender (upper chart) and without effects of age and gender (lower chart). Asterisks (*) represent a status that should be discriminated by the discriminant score.

The NC group had a significantly higher NC score than the patient groups ($p=1.7\times10^{-4}$) (FIG. 4A). The difference still remained after the effects of age and gender were removed ($p=1.9\times10^{-2}$) (FIG. 4A). The area under the ROC curve (AUC) indicated that the ability of the NC score to correctly discriminate between the NC group and the non- NC group was significant for both with and without effects of age and gender. Although NC individuals were cognitively and neurologically normal, those with low NC scores had atrophy in the brain (FIG. 5A).

Figure 5:
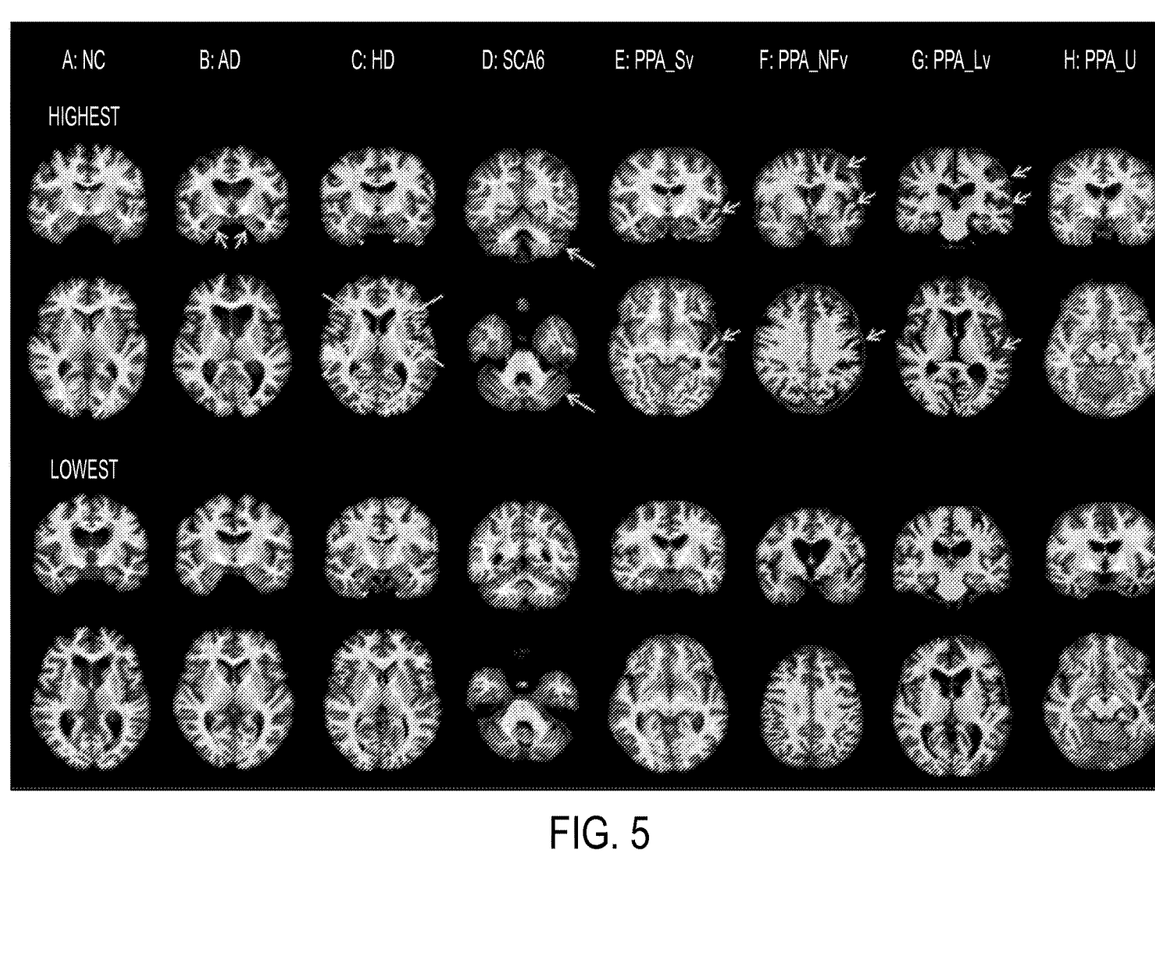
FIG. 5 depicts test images with the highest discriminant score (upper two rows) and the lowest discriminant score (lower two rows).

FIG. 5 depicts test images with the highest discriminant score (upper two rows) and the lowest discriminant score (lower two rows).

A: Ventricular enlargement was prominent in the NC participant with the lowest NC score.

B: The AD participant with the highest AD score showed prominent atrophy in the medial temporal area (yellow arrows), which was not seen in the AD participant with the lowest AD score.

C: The HD participant with the highest HD score (HD_es) showed prominent atrophy in the basal ganglia (yellow arrows), which was not seen in the HD_ffo participant with the lowest HD score.

D: The SCA6 participant with the highest SCA6 score showed prominent atrophy in the cerebellum (yellow arrows). Cerebellar atrophy was found only in the upper half of the cerebellum in the SCA6 participant with the lowest SCA6 score.

E: The PPA_Sv participant with the highest PPA_Sv score showed prominent atrophy in the anterior part of the left temporal lobe (yellow arrows), which was only mildly seen in the PPA_Sv participant with the lowest PPA_Sv score.

F: PPA_NFv participant with the highest PPA_NFv score showed prominent atrophy in the left perisylvian areas (yellow arrows), which was only mildly seen in the PPA_NFv participant with the lowest PPA_NFv score.

G: The PPA_Lv participant with the highest PPA_Lv score showed prominent atrophy in the left parieto-temporal area (yellow arrows), which was only mildly seen in the PPA_Lv participant with the lowest PPA_Lv score.

H: The PPA_U participant with the highest PPA_U score showed only mild ventricular enlargement. However, prominent atrophy in the anterior part of the temporal area (yellow arrows), similar to that in the PPA_Sv, was seen in the PPA_U participant with the lowest PPA_U score. Images are in radiological convention The AD scores of the AD and MCI groups were significantly higher than those of the non-AD non-MCI group ($p=1.6\times10^{-9}$ and $4.0\times10^{-2}$). The AD scores of the MCI_c group tended to be higher than those of the other groups, but did not reach statistical significance ($p=1.4\times10^{-1}$). After removing the effects of age and gender, the AD scores were still significantly higher in the AD group ($p=1.1\times10^{-7}$), but not in the MCI and MCI_c groups ($p=2.0\times10^{-1}$ and $1.8\times10^{-1}$). The AUC indicated that the ability of the AD score to correctly discriminate between the AD or MCI group and the non-AD non-MCI group was significant. In the AD group, the significance still remained after removing the effects of age and gender, but not in the MCI group (Table 2-II).

Medial temporal atrophy, which is typically seen in AD patients, was not apparent on AD images with a low AD score (FIG. 5B). There were significant correlations between the AD score and the MMSE, the ADAS, the CDR-rating, and the CDR-sum of box scores, but not between the AD score and GDS. After removing the effects of age and gender, the AD score still correlated with the MMSE, the ADAS, the CDR-rating, and the CDR-sum of box scores.

The HD scores of the HD groups (HD_es, HD_cto, and HD_ffo) were significantly higher than those of the non-HD group ($p=0.9\times10^{-2}$, $2.3\times10^{-4}$, and $2.2\times10^{-4}$). After removing the effects of age and gender, HD scores were still higher in the HD_cto and HD_ffo groups ($p=0.003$ and $0.002$), but the tendency toward higher HD scores for the HD_es group did not reach statistical significance ($p=0.096$). The AUC indicated that the ability of the HD score to correctly discriminate between the HD group (HD_es, HD_cto, and HD_ffo) and the non-HD group was significant. This significance remained after removing the effects of age and gender, except in HD_es, which was slightly below statistical significance (Table 2, III). Atrophy in the striatum, which is typically seen in HD patients, was not apparent in HD images with a low HD score (FIG. 5C). HD score did not correlate with MoCA score.

The SCA6 scores of the SCA6 group were significantly higher than those of the non-SCA6 group ($p=3.1\times10^{-15}$). After removing the effects of age and gender, the SCA6 score was still significantly higher in the SCA6 group ($p=1.2\times10^{-8}$). The AUC indicated that the ability of the SCA6 score to correctly discriminate between the SCA6 group and the non-SCA6 group was significant. The significance remained after removing the effects of age and gender (Table 2, IV). Atrophy in the cerebellum, which is typically seen in SCA6 patients, was only seen in the upper half of the cerebellum in SCA6 images with a low SCA6 score (FIG. 5D). The SCA6 score, with the effects of age and gender, was correlated with the SARA score, but the significance was less after removing the effects of age and gender.

The PPA_Sv score of the PPA_Sv group was significantly higher than that of the non-PPA_Sv group ($p=0.001$). The PPA_NFv score of the PPA_NFv group was significantly higher than that of the non-PPA_NFv group ($p=2.0\times10^{-7}$). The PPA_Lv score of the PPA_Lv group was significantly higher than that of the non-PPA_Lv group ($p=0.001$). The PPA_U group had a tendency toward higher PPA_U scores than those of the non-PPA_U group, but this did not reach statistical significance ($p=0.162$). After removing the effects of age and gender, these four PPA scores were all significantly higher in PPA groups ($P=0.001$, $4.1\times10^{-5}$, $0.006$, and $0.019$). The AUC indicated that the ability of the PPA score to correctly discriminate between the three PPA groups (PPA_Sv, PPA_NFv, and PPA_Lv) and the non-PPA group was significant. The significance remained after removing the effects of age and gender. However, the discrimination of the PPA_U group from the non-PPA_U group was not significant, either with or without the effects of age and gender. Typical anatomical features, such as atrophy in the left fronto-temporal area (PPA_Sv), atrophy in the left frontal operculum (PPA_NFv), and atrophy in the left temporo-parietal area (PPA_Lv), were not apparent in PPA_Sv, PPA_NFv, and PPA_Lv images with low PPA scores (FIGS. 5E-G). The WAB repetition scores correlated with the PPA_NFv scores only after removing the effects of age and gender, but a significant correlation was not identified between the WAB AQ score and any of the PPA scores.

4. Discussion

GAIA employs mismatches between a target image and the reference atlas to extract anatomical features. The most striking aging effect was found in the periventricular area, probably due to ventricular enlargement, as previously reported (Juva et al., 1993; Wang et al., 2013). The effect of gender is also in agreement with the results of past studies (Chen et al., 2007; Coffey et al., 1998; Thambisetty et al., 2010).

Rank order was used to quantify the intensity profile. For T1-weighted images, the intensity of the cerebrospinal fluid is always lower than that of gray and white matter, and the white matter intensity is always higher than that of gray matter. The comparison of NC scores among five different protocols indicated the robustness of the GAIA-based approach against protocol variability.

The feature vectors extracted from the training dataset agreed with known pathological hallmarks. The medial temporal lobe and the parietal lobe were negatively weighted in AD, the basal ganglia were positively weighted in HD, the cerebellum was negatively weighted in SCA6, the left temporal area was negatively weighted in PPA_Sv, the left frontal operculum and the insular were negatively weighted in PPA_NFv, and the left parieto-temporal area was negatively weighted in PPA_Lv, regardless of the effects of age and gender. Note that with GAIA, the rank of the areas with cortical atrophy decreases because of the inclusion of the dark cerebrospinal fluid signal, and the lenticular nuclei with atrophy were ranked higher because of the inclusion of the surrounding bright white matter signal.

Several features were observed in GAIA-based image scoring. First, the discriminant scores indicated "How close the target image was to the typical anatomical feature of the disease." As indicated by FIG. 5, the discriminant scores were not suitable to detect diseases in their early stage with only subtle anatomical alterations, or with atypical anatomical features. Second, AD, SCA6, PPA_Sv, and PPA_NFv were well discriminated from each other, which was expected from previous publications (Dolek et al., 2012; Laakso et al., 1998; Marigliano et al., 2013). Congruent with past studies that used morphometry (Xu et al., 2000), the AD score had limited power to separate MCI and MCI_c groups from non-AD, non-MCI groups. The AD, SCA6, and PPA_NFv scores correlated with functional scales, similar to the correlations between hippocampal volume and cognitive scales (Arlt et al., 2012; Troyer et al., 2012), between cerebellar volume and ataxia scales (Eichler et al., 2011; Jacobi et al., 2012; Jung et al., 2012), and between regional volumes and WAB subsets (Amici et al., 2007). This indicated that GAIA-based feature recognition is comparable to that based on morphometry. Third, the disease separation was generally better when the effects of age and gender were accounted for, probably because the age of the AD, MCI, MCI_c, and PPA groups was higher than that of the SCA6 and HD groups. Last, the performance of the discriminant scores was not satisfactory for the disease categories that included various histopathological diagnoses, or those with an atypical phenotype. MCI includes early AD and MCI without AD pathology (Albert, 2011). The histopathological diagnosis of PPA_Lv is usually AD (Kirshner, 2012; Rabinovici et al., 2008), which might partially explain the relatively high PPA_Lv score in AD and MCI_c, but the clinical phenotype is different from that of common AD. PPA_U is, by definition, a mixture of unclassified cases of PPA, which lacks common anatomical features.

While the GAIA was intended to be used as a tool for anatomical feature recognition, the natural extension is an automated image-based diagnosis. For such a diagnostic application, the GAIA needs to give discriminant scores with sufficiently high sensitivity and specificity for the diagnosis of individual patients. The ROC analysis demonstrated substantially high sensitivity and specificity for AD, HD_es, SCA6, PPA_Sv and PPA_NFv, suggesting the potential for a diagnostic application. However, given the fact that there are patients with less typical or atypical anatomical features (FIG. 5), GAIA alone might be insufficient for the clinical evaluation. One possibility for a future clinical application is a probabilistic evaluation of a single patient based on anatomical feature similarity. Namely, GAIA could be used to sort stored clinical cases with anatomical features similar to a target image, to calculate the probability of a given clinical condition, such as diagnosis, prognosis, or responsiveness to treatment. Anatomical features extracted by GAIA could also be combined with other clinical information, such as age, gender, symptoms, medical history, risk factors, results of physical examinations, and other neurological evaluations, to simulate physicians' decision-making. Since the effectiveness of combining image and non-image information to form a classification of AD and MCI has been demonstrated (Zhang et al., 2011), the GAIA might be a promising tool to extend the application of multimodal classification to a cohort that consists of multiple diseases and conditions. The exploration of the applicability of GAIA to clinical diagnosis support will be an important future direction.

In this study, GAIA was based on linear transformation, which does not require computationally extensive non-linear transformation. It is possible to combine GAIA with non-linear transformation. As the nonlinearity of the transformation increases, the accuracy of atlas-based structural definition also increases. However, the transformation results become highly sensitive to intensity abnormalities, potentially leading to unpredictable outcomes. The combination of GAIA and nonlinear transformation and the effect of the degree of nonlinearity are, thus, important directions for future research. The GAIA found characteristic anatomical features for each disease category, which has been previously reported by morphometric studies. Please note that conventional morphometry studies are based on manual delineation of pre-selected structures, or voxel-based analyses, which lead to voxel-based patterns specific to each disease on a study-specific (customized) template, while GAIA applies a single generic atlas and simple linear transformation for all disease models, making it an ideal tool for CBIR of a large clinical database.

A computing device may perform certain functions in response to a processor executing software instructions contained in a computer-readable medium, such as a memory. In alternative embodiments, hardwired circuitry may be used in place of or in combination with software instructions to implement features consistent with principles of the disclosure. Thus, implementations consistent with principles of the disclosure are not limited to any specific combination of hardware circuitry and software.

Exemplary embodiments may be embodied in many different ways as a software component. For example, it may be a stand-alone software package, a combination of software packages, or it may be a software package incorporated as a "tool" in a larger software product. It may be downloadable from a network, for example, a website, as a stand-alone product or as an add-in package for installation in an existing software application. It may also be available as a client-server software application, or as a web-enabled software application. It may also be embodied as a software package installed on a hardware device.

Numerous specific details have been set forth to provide a thorough understanding of the embodiments. It will be understood, however, that the embodiments may be practiced without these specific details. In other instances, well-known operations, components and circuits have not been described in detail so as not to obscure the embodiments. It can be appreciated that the specific structural and functional details are representative and do not necessarily limit the scope of the embodiments.

It is worthy to note that any reference to "one embodiment" or "an embodiment" means that a particular feature, structure, or characteristic described in connection with the embodiment is included in at least one embodiment. The appearances of the phrase "in one embodiment" in the specification are not necessarily all referring to the same embodiment.

Although some embodiments may be illustrated and described as comprising exemplary functional components or modules performing various operations, it can be appreciated that such components or modules may be implemented by one or more hardware components, software components, and/or combination thereof. The functional components and/or modules may be implemented, for example, by logic (e.g., instructions, data, and/or code) to be executed by a logic device (e.g., processor). Such logic may be stored internally or externally to a logic device on one or more types of computer-readable storage media.

Some embodiments may comprise an article of manufacture. An article of manufacture may comprise a storage medium to store logic. Examples of a storage medium may include one or more types of computer-readable storage media capable of storing electronic data, including volatile memory or non-volatile memory, removable or non-removable memory, erasable or non-erasable memory, writeable or re-writeable memory, and so forth. Examples of storage media include hard drives, disk drives, solid state drives, and any other tangible or non-transitory storage media.

It also is to be appreciated that the described embodiments illustrate exemplary implementations, and that the functional components and/or modules may be implemented in various other ways which are consistent with the described embodiments. Furthermore, the operations performed by such components or modules may be combined and/or separated for a given implementation and may be performed by a greater number or fewer number of components or modules.

Some of the figures may include a flow diagram. Although such figures may include a particular logic flow, it can be appreciated that the logic flow merely provides an exemplary implementation of the general functionality. Further, the logic flow does not necessarily have to be executed in the order presented unless otherwise indicated. In addition, the logic flow may be implemented by a hardware element, a software element executed by a processor, or any combination thereof.

While various exemplary embodiments have been described above, it should be understood that they have been presented by way of example only, and not limitation. Thus, the breadth and scope of the present disclosure should not be limited by any of the above-described exemplary embodiments, but should instead be defined only in accordance with the following claims and their equivalents.

The invention claimed is:

1. A computer-implemented method for recognizing gross features from a region of interest of a subject, comprising:
   receiving an image comprising a plurality of image elements representing the region of interest of the subject to a data storage device;
   co-registering, using at least one data processor, the image to an atlas to segment the plurality of image elements into a plurality of sub-regions corresponding to structures in the atlas, wherein the structures in the atlas are ordered in a first rank order according to a predetermined feature of the structures;
   ordering, using the at least one data processor, the plurality of sub-regions in a second rank order according to the predetermined feature; and
   identifying as gross features one or more of the plurality of sub-regions whose positions in the second rank order of the ordered sub-regions differ from positions in the first rank order of the corresponding ordered structures in the atlas,
   wherein the gross features are sub-regions whose positions in the second rank order differ from the positions in the first rank order of the corresponding structures in the atlas by at least three positions.

2. The method of claim 1, wherein the gross features are sub-regions whose positions in the second rank order differ from the positions in the first rank order of the corresponding structures in the atlas by a statistically significant number of positions.

3. The method of claim 1, wherein the predetermined feature is a measure of intensity.

4. The method of claim 3, wherein the measure of intensity is at least one of:
   a mean intensity of the image elements in each sub-region;
   a sum of intensities of the image elements in each sub-region;
   a highest intensity of the image elements in each sub-region; and
   a lowest intensity of the image elements in each sub-region.

5. The method of claim 1, wherein the predetermined feature is at least one texture parameter.

6. The method of claim 5, wherein the at least one texture parameter is one of histogram, absolute gradient, run-length matrix, co-occurrence matrix, auto-regressive model, and wavelets.

7. The method of claim 1, wherein the image is generated from at least one of magnetic resonance imaging (MRI), computed tomography (CT), positron emission tomography (PET), ultrasound, or nuclear tracer three-dimensional imaging.

8. The method of claim 1, wherein the plurality of image elements are pixels or voxels.

9. The method of claim 1, wherein the region of interest comprises a portion of at least one of a brain, a heart, a liver, skin, a lung, another organ, one or more bones, or any combination thereof.

10. A computer-implemented method for recognizing gross features from a region of interest of a subject, comprising:
   receiving an image comprising a plurality of image elements representing the region of interest of the subject to a data storage device;
   co-registering, using at least one data processor, the image to an atlas to segment the plurality of image elements into a plurality of sub-regions corresponding to structures in the atlas, wherein the structures in the atlas are ordered in a first rank order according to a predetermined feature of the structures;
   ordering, using the at least one data processor, the plurality of sub-regions in a second rank order according to the predetermined feature; and
   identifying as gross features one or more of the plurality of sub-regions whose positions in the second rank order of the ordered sub-regions differ from positions in the first rank order of the corresponding ordered structures in the atlas,
   wherein:
      the predetermined feature is at least one texture parameter; and
      the ordering is based on scalar values that are extracted from the at least one texture parameter.

11. The method of claim 1, wherein the image is co-registered to the atlas using a linear and/or nonlinear transformation.

12. A computer-implemented method for recognizing gross features from a region of interest of a subject, comprising:
  receiving an image comprising a plurality of image elements representing the region of interest of the subject to a data storage device;
  co-registering, using at least one data processor, the image to an atlas to segment the plurality of image elements into a plurality of sub-regions corresponding to structures in the atlas, wherein the structures in the atlas are ordered in a first rank order according to a predetermined feature of the structures;
  ordering, using the at least one data processor, the plurality of sub-regions in a second rank order according to the predetermined feature;
  identifying as gross features one or more of the plurality of sub-regions whose positions in the second rank order of the ordered sub-regions differ from positions in the first rank order of the corresponding ordered structures in the atlas; and
  creating a feature vector storing identifiers of the ordered plurality of sub-regions, wherein placement in the feature vector indicates a position of sub-regions in the order.

13. The method of claim 12, further comprising:
  identifying a second feature vector whose correlation with the feature vector exceeds a threshold, wherein the second feature vector is associated with the region of interest of another subject and an anatomical feature of the another subject; and
  providing a likelihood that the subject has the anatomical feature.

14. The method of claim 13, wherein the anatomical feature is at least one of an abnormality, a disease, a condition, a diagnosis, or any combination thereof.

15. A computer system for recognizing gross features from a region of interest of a subject, the computer system comprising:
  a memory storing computer-executable instructions; and
  at least one data processor that is coupled to the memory and that is configured to execute the computer-executable instructions to:
    receive an image comprising a plurality of image elements representing the region of interest of the subject;
    co-register the image to an atlas to segment the plurality of image elements into a plurality of sub-regions corresponding to structures in the atlas, wherein the structures in the atlas are ordered in a first rank order according to a predetermined feature of the structures;
    order the plurality of sub-regions in a second rank order according to the predetermined feature; and
    identify as gross features one or more of the plurality of sub-regions whose positions in the first rank order of the ordered sub-regions differ from positions in the second rank order of the corresponding ordered structures in the atlas,
    wherein the gross features are sub-regions whose positions in the second rank order differ from the positions in the first rank order of the corresponding structures in the atlas by at least three positions.

16. The computer system of claim 15, wherein the gross features are sub-regions whose positions in the second rank order differ from the positions in the first rank order of the corresponding structures in the atlas by a statistically significant number of positions.

17. The computer system of claim 15, wherein the predetermined feature is a measure of intensity.

18. The computer system of claim 17, wherein the measure of intensity is at least one of:
  a mean intensity of the image elements in each sub-region;
  a sum of intensities of the image elements in each sub-region;
  a highest intensity of the image elements in each sub-region; and
  a lowest intensity of the image elements in each sub-region.

19. The computer system of claim 15, wherein the predetermined feature is at least one texture parameter.

20. The computer system of claim 19, wherein the at least one texture parameter is one of histogram, absolute gradient, run-length matrix, co-occurrence matrix, auto-regressive model, and wavelets.

21. The computer system of claim 15, wherein the image is co-registered to the atlas using a linear and/or nonlinear transformation.

22. The computer system of claim 15, wherein the image is generated from at least one of magnetic resonance imaging (MRI), computed tomography (CT), positron emission tomography (PET), ultrasound, or nuclear tracer three-dimensional imaging.

23. The computer system of claim 15, wherein the plurality of image elements are pixels or voxels.

24. The computer system of claim 15, wherein the region of interest comprises a portion of at least one of a brain, a heart, a liver, skin, a lung, another organ, one or more bones, or any combination thereof.

25. A computer system for recognizing gross features from a region of interest of a subject, the computer system comprising:
  a memory storing computer-executable instructions; and
  at least one data processor that is coupled to the memory and that is configured to execute the computer-executable instructions to:
    receive an image comprising a plurality of image elements representing the region of interest of the subject;
    co-register the image to an atlas to segment the plurality of image elements into a plurality of sub-regions corresponding to structures in the atlas, wherein the structures in the atlas are ordered in a first rank order according to a predetermined feature of the structures;
    order the plurality of sub-regions in a second rank order according to the predetermined feature; and
    identify as gross features one or more of the plurality of sub-regions whose positions in the first rank order of the ordered sub-regions differ from positions in the second rank order of the corresponding ordered structures in the atlas,
    wherein:
      the predetermined feature is at least one texture parameter; and
      the ordering is based on scalar values that are extracted from the at least one texture parameter.

26. A computer system for recognizing gross features from a region of interest of a subject, the computer system comprising:
  a memory storing computer-executable instructions; and at least one data processor that is coupled to the memory and that is configured to execute the computer-executable instructions to:
  receive an image comprising a plurality of image elements representing the region of interest of the subject;
  co-register the image to an atlas to segment the plurality of image elements into a plurality of sub-regions corresponding to structures in the atlas, wherein the structures in the atlas are ordered in a first rank order according to a predetermined feature of the structures;
  order the plurality of sub-regions in a second rank order according to the predetermined feature;
  identify as gross features one or more of the plurality of sub-regions whose positions in the first rank order of the ordered sub-regions differ from positions in the second rank order of the corresponding ordered structures in the atlas; and
  create a feature vector storing identifiers of the ordered plurality of sub-regions, wherein placement in the feature vector indicates a position of sub-regions in the order.

27. The computer system of claim 26, further comprising:
  identifying a second feature vector whose correlation with the feature vector exceeds a threshold, wherein the second feature vector is associated with the region of interest of another subject and an anatomical feature of the another subject; and
  providing a likelihood that the subject has the anatomical feature.

28. The computer system of claim 27, wherein the anatomical feature is at least one of an abnormality, a disease, a condition, a diagnosis, or any combination thereof.

29. A non-transitory computer readable storage medium for recognizing gross features from a region of interest of a subject, the computer readable storage medium comprising instructions that when executed enables a computing system to:
  receive an image comprising a plurality of image elements representing the region of interest of the subject;
  co-register the image to an atlas to segment the plurality of image elements into a plurality of sub-regions corresponding to structures in the atlas, wherein the structures in the atlas are ordered in a first rank order according to a predetermined feature;
  order the plurality of sub-regions in a second rank order according to the predetermined feature; and
  identify as gross features one or more of the plurality of sub-regions whose positions in the first rank order of the ordered sub-regions differ from positions in the second rank order of the corresponding ordered structures in the atlas,
  wherein the gross features are sub-regions whose positions in the second rank order differ from the positions in the first rank order of the corresponding structures in the atlas by at least three positions.

30. The non-transitory computer readable storage medium of claim 29, wherein the gross features are sub-regions whose positions in the second rank order differ from the positions in the first rank order of the corresponding structures in the atlas by a statistically significant number of positions.

31. The non-transitory computer readable storage medium of claim 29, wherein the predetermined feature is a measure of intensity.

32. The non-transitory computer readable storage medium of claim 31, wherein the measure of intensity is at least one of:
  a mean intensity of the image elements in each sub-region;
  a sum of intensities of the image elements in each sub-region;
  a highest intensity of the image elements in each sub-region; and
  a lowest intensity of the image elements in each sub-region.

33. The non-transitory computer readable storage medium of claim 29, wherein the predetermined feature is at least one texture parameter.

34. The non-transitory computer readable storage medium of claim 33, wherein the at least one texture parameter is one of histogram, absolute gradient, run-length matrix, co-occurrence matrix, auto-regressive model, and wavelets.

35. The non-transitory computer readable storage medium of claim 29, wherein the image is co-registered to the atlas using a linear and/or nonlinear transformation.

36. The non-transitory computer readable storage medium of claim 29, wherein the image is generated from at least one of magnetic resonance imaging (MRI), computed tomography (CT), positron emission tomography (PET), ultrasound, or nuclear tracer three-dimensional imaging.

37. The non-transitory computer readable storage medium of claim 29, wherein the plurality of image elements are pixels or voxels.

38. The non-transitory computer readable storage medium of claim 29, wherein the region of interest comprises a portion of at least one of a brain, a heart, a liver, skin, a lung, another organ, one or more bones, or any combination thereof.

39. A non-transitory computer readable storage medium for recognizing gross features from a region of interest of a subject, the computer readable storage medium comprising instructions that when executed enables a computing system to:
  receive an image comprising a plurality of image elements representing the region of interest of the subject;
  co-register the image to an atlas to segment the plurality of image elements into a plurality of sub-regions corresponding to structures in the atlas, wherein the structures in the atlas are ordered in a first rank order according to a predetermined feature;
  order the plurality of sub-regions in a second rank order according to the predetermined feature; and
  identify as gross features one or more of the plurality of sub-regions whose positions in the first rank order of the ordered sub-regions differ from positions in the second rank order of the corresponding ordered structures in the atlas,
  wherein:
    the predetermined feature is at least one texture parameter; and
    the ordering is based on scalar values that are extracted from the at least one texture parameter.

40. A non-transitory computer readable storage medium for recognizing gross features from a region of interest of a subject, the computer readable storage medium comprising instructions that when executed enables a computing system to:
  receive an image comprising a plurality of image elements representing the region of interest of the subject;
  co-register the image to an atlas to segment the plurality of image elements into a plurality of sub-regions corresponding to structures in the atlas, wherein the structures in the atlas are ordered in a first rank order according to a predetermined feature;

order the plurality of sub-regions in a second rank order according to the predetermined feature;

identify as gross features one or more of the plurality of sub-regions whose positions in the first rank order of the ordered sub-regions differ from positions in the second rank order of the corresponding ordered structures in the atlas; and create a feature vector storing identifiers of the ordered plurality of sub-regions, wherein placement in the feature vector indicates a position of sub-regions in the order.

41. The method of claim 40, wherein the computer readable storage medium further comprises instructions that when executed enables the computing system to:

identifying a second feature vector whose correlation with the feature vector exceeds a threshold, wherein the second feature vector is associated with the region of interest of another subject and an anatomical feature of the another subject; and providing a likelihood that the subject has the anatomical feature.

42. The non-transitory computer readable storage medium of claim 41, wherein the anatomical feature is at least one of an abnormality, a disease, a condition, a diagnosis, or any combination thereof.

* * * * *

UNITED STATES PATENT AND TRADEMARK OFFICE
CERTIFICATE OF CORRECTION

PATENT NO. : 10,147,189 B2
APPLICATION NO. : 15/101779
DATED : December 4, 2018
INVENTOR(S) : Miller et al.

Page 1 of 1

It is certified that error appears in the above-identified patent and that said Letters Patent is hereby corrected as shown below:

In the Specification

Column 1, Line 14-25, Replace the second paragraph as follows:
STATEMENT OF GOVERNMENTAL INTEREST
This invention was made with government support under DC011317, AG033774, DA061427, NS056883, EB015909, RR021382, EB000195, AG020012, EY015802, NS059830, RR000052, NS056307, NS068897, AG005146, RR003061, awarded by the National Institutes of Health. The government has certain rights in the invention.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*